(12) United States Patent
Soper et al.

(10) Patent No.: US 6,479,700 B2
(45) Date of Patent: Nov. 12, 2002

(54) METHOD FOR SEPARATING A BASIC AMINO ACID FROM FERMENTATION BROTH

(75) Inventors: John Soper, Mt. Zion, IL (US); Ahmad K. Hilaly, Springfield, IL (US); Kevin Moore, Mt. Zion, IL (US); Thomas P. Binder, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 09/808,123

(22) Filed: Mar. 15, 2001

(65) Prior Publication Data
US 2002/0035269 A1 Mar. 21, 2002

Related U.S. Application Data
(60) Provisional application No. 60/263,228, filed on Jan. 23, 2001, and provisional application No. 60/192,891, filed on Mar. 29, 2000.

(51) Int. Cl.[7] .................. C07C 227/00; C07C 229/00
(52) U.S. Cl. .......................... 562/554; 562/553
(58) Field of Search ................. 562/553, 554

(56) References Cited

U.S. PATENT DOCUMENTS

| | | | |
|---|---|---|---|
| 2,985,589 A | 5/1961 | Broughton et al. | 210/34 |
| 4,714,767 A | 12/1987 | Tanaka et al. | 548/344 |
| 5,684,190 A | 11/1997 | Fechter et al. | 562/554 |

FOREIGN PATENT DOCUMENTS

| | | |
|---|---|---|
| EP | 0 337 440 | 10/1989 |
| FR | 2 666 996 | 3/1992 |
| JP | 62-292750 | * 12/1987 |

OTHER PUBLICATIONS

Aldrich Catalog Handbook of Fine Chemicals, p. 1023 (1998). Sigma–Aldrich Fine Chemicals.*
Derwent WPI Acession No. 9033885, English–language abstract for French Patent Publication NO. FR 2 666 996 from Dialog file 351.
Derwent WPI Acession No. 9401517, English–language abstract for European Patent Publication No. EP 0 533 039 from Dialog file 351.
Barker, P.E., and Deeble, R.E., "Sequential Chromatographic Equipment for the Separation of a Wide Range of Organic Mixtures," *Chromatographia* 8:67–79, Pergamon Press (1975).
Morgart, J.R., and Graaskamp, J.M., "Continuous Process Scale Chromatography," *Pittsburgh Conference on Analytical Chemistry and Applied Spectroscopy*, Paper No. 230, New Orleans, LA (Feb. 22, 1988).
Van Walsem, H.J., and Thompson, M.C., "Simulated moving bed in the production of lysine," *J. Biotechnol.* 59:127–132, Elsevier Science B.V. (1997).

* cited by examiner

*Primary Examiner*—Mukund J. Shah
*Assistant Examiner*—Zachary C. Tucker
(74) *Attorney, Agent, or Firm*—Sterne, Kessler, Goldstein & Fox P.L.L.C.

(57) ABSTRACT

This invention relates to a method for separating basic amino acids from fermentation broth comprising contacting the broth with strong acid cation exchange resins that have a low degree of cross-linkage and eluting the amino acid. The method described herein results in higher yield and higher purity of lysine, in addition to higher throughput, as compared to conventional processes of purification of lysine from fermentation broth.

15 Claims, 1 Drawing Sheet

METHOD FOR SEPARATING A BASIC AMINO ACID FROM FERMENTATION BROTH

CROSS-REFERENCE TO RELATED APPLICATIONS

Figure 1:
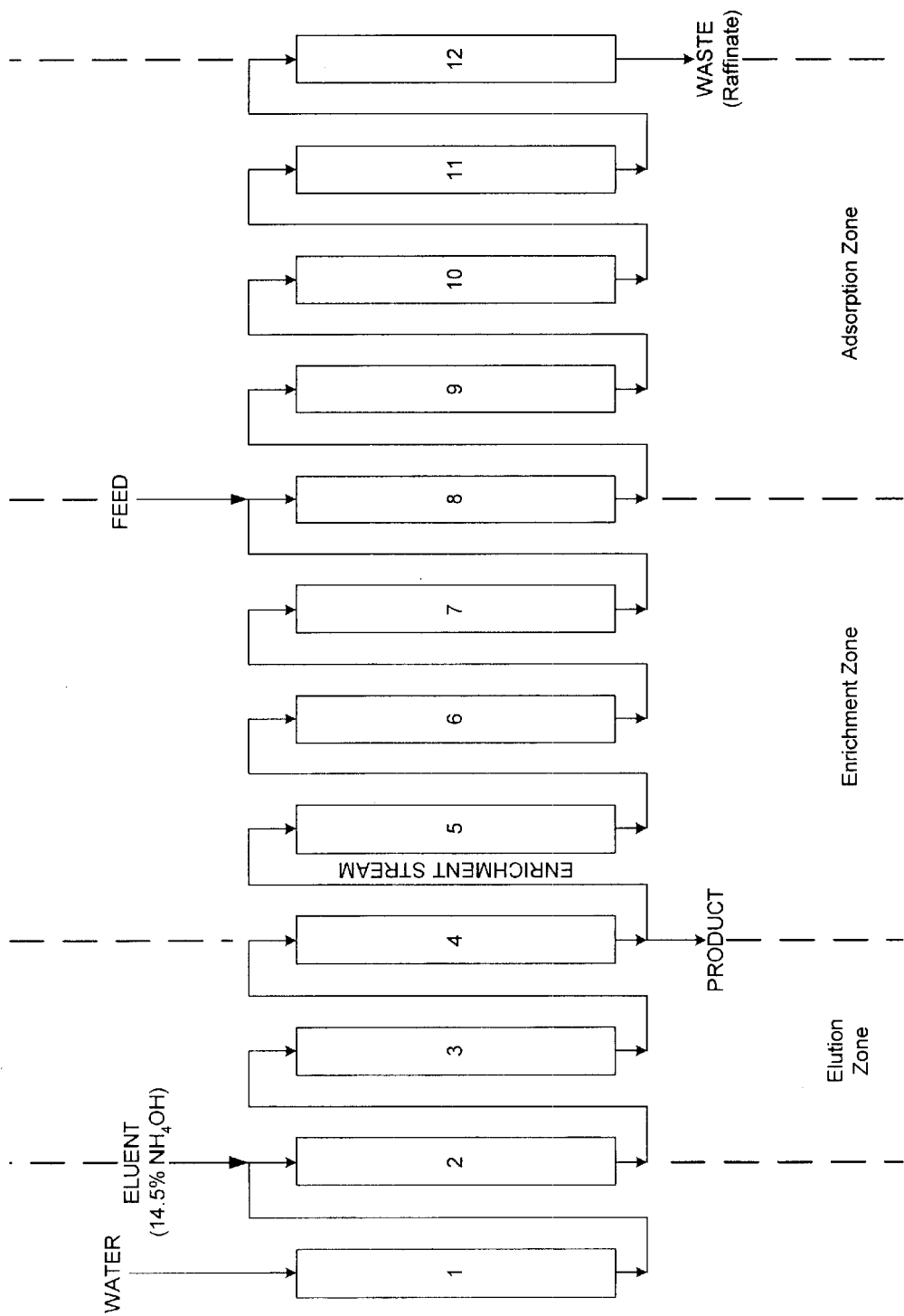

This non-provisional application is related to provisional application No. 60/263,228, filed Jan. 23, 2001 and No. 60/192,891, filed Mar. 29, 2000, the content of which is incorporated herein by reference.

BACKGROUND OF THE INVENTION

1. Field of the Invention

The present invention relates to a method for separating a basic amino acid from a fermentation broth.

2. Background Art

Lysine and other basic amino acids are used extensively as animal feed supplements. Typically, lysine is produced by the fermentation of dextrose. In addition to lysine, the fermentation broth contains a variety of impurities, such as color bodies, residual sugars, salts, and other by-products. The primary step in the purification of lysine from fermentation broth is ion exchange chromatography (Tanaka, et al., U.S. Pat. No. 4,714,767 (1985)). The chromatographic separation can be operated in batch or continuous mode using fixed bed or simulated moving bed technology (Van Walsern, H. J., and Thompson, M. C., J. Biotechnol., 59:127–132. (1997)). Typically strong acid cation exchange resins with a high degree of cross-linkage are used.

Simulated moving bed (SMB) technology is a convenient and efficient method of chromatographic separation of fermentation broth (Broughton, D. B., U.S. Pat. No. 2,985,589 (1961)). When traditional strong acid cation exchange resins, with a high degree of cross-linkage, are used in SMB operation, the purity of lysine obtained is only 80–85%, with a yield of about 85–90%. This low level of separation obtained with traditional strong acid cation exchange resins that have a high degree of cross-linkage may not be satisfactory for industrial-scale production. There is therefore a need to improve the purity and yield of lysine during the purification of fermentation broth.

BRIEF SUMMARY OF THE INVENTION

The present invention relates to a method for separating a basic amino acid from fermentation broth using simulated moving bed technology, comprising contacting the fermentation broth with strong acid cation exchange resins that have a low degree of cross-linkage, and eluting the amino acids from the exchange resins.

BRIEF DESCRIPTION OF THE DRAWINGS/FIGURES

FIG. 1 shows the column configuration of amino acid separation in simulated moving bed operation.

DETAILED DESCRIPTION OF THE INVENTION

The present invention relates to method and apparatus of separating basic amino acids from a fermentation broth. Specifically, the invention relates to separating basic amino acids from fermentation broth, using simulated moving bed technology, comprising: (a) contacting the fermentation broth with strong acid cation exchange resins that have a low degree of cross-linkage; and (b) eluting the basic amino acids from the exchange resins such that the basic amino acids are separated from the original fermentation broth.

The method of the current invention utilizes a simulated moving bed (SMB) apparatus. SMB apparatus comprise multiple columns containing ion exchange resins are connected in series as shown in FIG. 1. Preferably, the locations of entry ports for feed and eluent, as well as the exit ports for product and raffinate, are changed periodically in the direction of the fluid flow in order to simulate counter current movement of resins with respect to the fluids. Preferably, a portion of the product stream is recycled (known as enrichment stream) back to the apparatus at the port next to the product exit port. The ports divide the apparatus into multiple zones. Preferably, the apparatus consists of three zones, namely, the adsorption zone, the enrichment zone, and the elution zone. The adsorption zone includes the columns between feed entry port and raffinate exit port. The elution zone consists of columns between eluent entry port and product exit port. The columns between the enrichment entry port and feed entry port constitute the enrichment zone. A 4-th zone, known as reload zone, is often used in order to minimize the solvent usage. There are a few types of SMB apparatus commercially available. These apparatus can be divided into two categories, namely, moving port system and moving column system (Barker, P. E. and Deeble, R. E., *Chromatographia* 8:67–69 (1975)). The SORBEX system developed by UOP (Universal Oil Products Inc.) is an example of moving port system. Examples of moving column systems are the ADSEP system (Morgart, J. R. and Graaskamp, J. M., "Continuous Process Scale Chromatography," *Pittsburg Conference on Analytical Chemistry and Applied Spectroscopy, Paper No.* 230, New Orleans, La. (Feb. 22, 1988)) developed by Illinois Water Treatment (IWT), and the ISEP system (Rossiter, G. J., "ISEP, A Moving Bed Contractor for Chromatographic Separations," *Fourth Workshop on Preparative HPLC*, Salzburg, Austria (Mar. 28, 1993)) developed by Advanced Separation Technologies, Inc. (AST).

A preferred embodiment of the present invention provides a method for separating basic amino acids from fermentation broth. Examples of fermentation broths include but are not limited to liquors, or broths derived from beet molasses, cane molasses, or hydrolysates of starch or soy protein. Any of the fermentation broths may be filtered, or unfiltered.

The present invention relates to methods for separating basic amino acids from fermentation broth using strong acid cation exchange resins with low cross-linkage. Preferably, the present invention relates to strong acid cation exchange resins that are cross-linked less than about 8%. More preferably, the method of the present invention employs strong acid cation exchange resins that are cross-linked from about 2 to 7%. Most preferably, the method of the present invention employs strong acid cation exchange resins that are cross-linked from about 4 to 6.5%, preferably about 4% or about 6.5%. Examples of strong acid cation exchange resins with a low degree of cross-linkage include, but are not limited to, SK104 (Mitsubishi), 4% cross-linkage, and GC480 (Finex), 6.5% cross-linkage.

The current invention provides a method for separating basic amino acids from fermentation broth using a simulated moving bed apparatus, comprising contacting the fermentation broth with strong acid cation exchange resins with a low degree of cross-linking and an elution step. Preferably, the elution step of the present invention comprises using about 1 to 7% $NH_4OH$, more preferably about 2 to 5.1%, most preferably about 2.2%. A preferred embodiment of the present invention provides an elution step comprising an elution volume of less than about 3 bed-volumes. More preferably, the elution step of the present invention comprises an elution volume of about 1 to 2 bed volumes. Most preferably, the elution step of the present invention comprises about 1.2 bed volumes. The method of the current invention, using strong acid cation exchange resins with a low degree of cross-linkage in a simulated moving bed apparatus, does not increase time for elution of the basic amino acids, as compared to higher cross-linked resins.

Another preferred embodiment of the present invention provides a method for separating basic amino acids from fermentation broth. As used herein, the term basic amino acid is used to mean any amino acid (natural, synthetic or modified) that has a positive charge at a neutral pH. Preferably, the basic amino acids of the current invention that are separated from the fermentation broth are selected from the group comprising arginine, histidine and lysine. More preferably, the present invention provides for separating lysine from fermentation broth.

When utilized in conjunction with SMB technology, strong acid cation exchange resins with a low degree of cross linkage have advantageous properties of higher dynamic capacity, faster exchange reaction rates and higher peak separation than the conventional basic amino acid separation resins with high cross-linkage. The combined effect of the unique properties of the strong acid cation exchange resins with a low degree of cross-linkage enable these resins to separate basic amino acids, specifically lysine, more effectively from fermentation broth. Operations using a simulated moving bed apparatus utilizing strong acid cation exchange resins with a low degree of cross-linkage result in higher throughput and higher concentration ratios as compared to operations using resins with a higher degree of cross-linkage. Furthermore, operations using a simulated moving bed apparatus utilizing strong acid cation exchange resins that have a low degree of cross-linking clearly show improved separation with higher yield and higher purity, as compared to experiments using resins with a higher degree of cross-linkage. A preferred embodiment of the present invention provides a method for lysine separation from a fermentation broth resulting in the basic amino acid being about 85% or greater pure. More preferably, the purity of the basic amino acid from the separation method is about 86 to 100%, most preferably about 85%, 93% or 95%. A preferred embodiment of the present invention provides a method for lysine separation from a fermentation broth resulting in a product yield of about 94% or greater of the basic amino acid. More preferably, the basic amino acid product yield is about 98% or greater, most preferably about 98% or 100%.

Experiments using a simulated moving bed apparatus that employ strong acid cation exchange resins that have a low degree of cross-linking clearly show improved concentration ratios, as compared to experiments using resins with a higher degree of cross-linkage. A preferred embodiment of the present invention provides a method for separation of a basic amino acid from a fermentation broth resulting in a concentration ratio of the basic amino acid being about 0.8 to 2.0. More preferably, the concentration ratio of the basic amino acid from is about 1.0 to 1.8. As used herein, the term concentration ratio is defined as the concentration of the basic amino acid in the product, divided by the concentration of the basic amino acid in the feed.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLE

The resins used in this work were divided into two categories based on the degree of cross-linkage. Included in the first category were resins with a level of cross-linkage 8% and higher, termed HX (high cross-linkage) resins. These resins are traditionally used in conventional lysine separation processes. Examples of HX resins are C100/1633 (Purolite) and T311 (Thermax). In the second category were resins with a level of cross-linkage lower than 8%, termed LX (low cross-linkage) resins. Examples of LX resins are SK104 (Mitsubishi) and GC480 (Finex).

Simulated Moving Bed Operation. Simulated moving bed (SMB) experiments were conducted in 12 columns loaded with 300 ml of strong cation exchange resins and arranged in series with the configuration as shown in FIG. 1. The flow rates of water and 14.5% of $NH_4OH$ were 6 cc/min and 33 cc/min respectively. Therefore, the concentration of $NH_4OH$ solution was 2.2% for eluting the adsorbed lysine. A step of 9 minutes, equivalent to a resin flow rate of 33.3 ml/min, was used for all the experiments. The operations were carried out at ambient temperature. Filtered fermentation broth, containing about 120 g/L lysine-HCl, was used as the feed material. The flow rates of feed and product stream were manipulated to achieve desirable separations.

Results. The HX and LX resins were evaluated in the SMB system at two levels of processing capacity. The higher level (HL) of processing refers to 8.0–8.4 gal/day of feed. The lower level (LL) of processing refers to 5.4–6.1 gal/day of feed. Table I compares the effectiveness of HX and LX resins in separating lysine from fermentation broths when the SMB was operated at HL level.

TABLE I

| Resin Category | HX | | LX | |
| --- | --- | --- | --- | --- |
| Resin | T311 | C100 | GC480 | SK104 |
| Cross-linkage (%) | 11.0 | 8.0 | 6.5 | 4.0 |
| Product Purity (%) | 85 | 74 | 85 | 85 |
| Product Yield (%) | 77 | 90 | 100 | 98 |
| Concentration Ratio* | 0.89 | 0.75 | 1.12 | 1.09 |
| Product Flow Rate (gal/day) | 8.8 | 8.8 | 7.2 | 6.8 |
| Raffinate Flow Rate (gal/day) | 9.5 | 13.3 | 15.9 | 17.5 |
| Feed Processing Capacity (gal/day) | 8.0 | 8.0 | 8.4 | 8.4 |

*Concentration Ratio = (Concentration of lysine in product)/(Concentration of lysine in feed).

Table I shows that LX resins produced significantly higher yields than HX resins. The concentration ratios attained with LX resins were also higher than those with HX resins, and the lysine concentration in the product, obtained from LX resins, was higher than the feed stream. This is a significant benefit since it will reduce the cost of subsequent evaporation.

When the SMB was operated at LL level with LX resins, part of the product stream was recycled and mixed with the fresh feed in the ratio of 1:2 by volume. The recycle rate was 2.7–3.0 gal/day whereas the fresh feed rate was 5.4–6.1 gal/day. Therefore, with this arrangement, the same amount of fresh feed was added to the SMB system both with the LX and HX resins. Table II compares the effectiveness of HX and LX resins in separating lysine from fermentation broths when the SMB was operated at LL level.

TABLE II

| Resin Category | HX | | LX | |
|---|---|---|---|---|
| Resin | T311 | C100 | GC480 | SK104 |
| Cross-linkage (%) | 11.0 | 8.0 | 6.5 | 4.0 |
| Product Purity (%) | 85 | 84 | 95 | 93 |
| Product Yield (%) | 91 | 93 | 100 | 98 |
| Concentration Ratio* | 0.68 | 0.72 | 1.53 | 1.72 |
| Product Flow Rate (gal/day) | 8.8 | 8.4 | 5.3 | 4.6 |
| Raffinate Flow Rate (gal/day) | 12.2 | 11.8 | 17.1 | 18.3 |
| Processing Capacity (gal/day) | 6.1 | 6.1 | 5.4 | 5.8 |

*Concentration Ratio = (Concentration of lysine in product)/(Concentration of lysine in feed).

Table II shows that the LX resins produced lysine product with higher yield and higher purity as compared to the HX resins. Most significantly, the values of concentration ratio attained with LX resins were considerably higher than those values attained with HX resins. Traditional SMB processes always result in a decreasing lysine concentration in the product stream, however, using resins with a low degree of cross-linking, the concentration ratios are increased in the product stream. As before, the higher dynamic capacity and faster uptake rate of the LX resins allowed higher fluid velocities in the adsorption zone of the SMB system with minimal loss of lysine in the waste stream. Also, in the case of LX resins, the relatively pure recycle stream added to the fresh feed lowered the overall impurity level of the mixed feed. All these factors jointly contributed to the significant improvements in the separation of lysine from fermentation broth, in terms of higher yield and purity of the lysine product.

What is claimed is:

1. A method of separating a basic amino acid from fermentation broth comprising:
    (a) contacting a fermentation broth with strong acid cation exchange resins in a simulated moving bed apparatus having at least an adsorption zone, and enrichment zone, and an elution zone, wherein said resins have a low degree of cross-linkage; and
    (b) eluting said amino acid from said exchange resins, such that said basic amino acid is separated from said fermentation broth.

2. The method of claim 1, wherein said strong acid cation exchange resins are cross-linked less than about 8%.

3. The method of claim 2, wherein said strong acid cation exchange resins are cross-linked from about 2% to about 7%.

4. The method of claim 1, wherein said elution step comprises using an elution volume less than about 3 bed-volumes.

5. The method of claim 4, wherein said elution step comprises using an elution volume from about 1 bed-volume to about 2 bed-volumes.

6. The method of claim 4, wherein said elution step comprises using an elution volume of about 1.2 bed-volumes.

7. The method of claim 1, wherein said elution step comprises using from about 1% to about 7% $NH_4OH$.

8. The method of claim 7, wherein said elution step comprises using from about 2% to about 5% $NH_4OH$.

9. The method of claim 1, wherein said basic amino acid is separated from said fermentation broth at a purity greater than about 85%.

10. The method of claim 9, wherein said basic amino acid is separated from said fermentation broth at a purity greater than about 90%.

11. The method of claim 1, wherein said basic amino acid is separated from said fermentation broth at a concentration ratio from about 0.8 to about 2.0.

12. The method of claim 11, wherein said basic amino acid is separated from said fermentation broth at a concentration ratio from about 1.0 to about 1.8.

13. The method of claim 1, wherein said basic amino acid is selected from the group consisting of natural basic amino acids, synthetic basic amino acids, and modified basic amino acids.

14. The method of claim 1, wherein said basic amino acid is selected from the group consisting of lysine, arginine and histidine.

15. The method of claim 14, wherein said amino acid is lysine.

* * * * *